US005258290A

United States Patent [19]

Weber et al.

[11] Patent Number: 5,258,290

[45] Date of Patent: Nov. 2, 1993

[54] **FERMENTATION PROCESS FOR THE PRODUCTION OF β-CARBOLINE DERIVATIVES BY *MYROTHECIUM VERRUCARIA***

[75] Inventors: Alfred Weber; Mario Kennecke; Jean C. Hilscher; Klaus Nickisch, all of Berlin, Fed. Rep. of Germany

[73] Assignee: Schering Aktiengesellschaft, Berlin, Fed. Rep. of Germany

[21] Appl. No.: 867,702

[22] PCT Filed: Aug. 1, 1991

[86] PCT No.: PCT/DE91/00626

§ 371 Date: Jul. 9, 1992

§ 102(e) Date: Jul. 9, 1992

[87] PCT Pub. No.: WO92/05269

PCT Pub. Date: Apr. 2, 1992

[30] Foreign Application Priority Data

Sep. 13, 1990 [DE] Fed. Rep. of Germany ....... 4029389

[51] Int. Cl.$^5$ ........................ C12P 17/18; C12P 01/02

[52] U.S. Cl. ..................................... 435/119; 435/171

[58] Field of Search .................. 435/119, 171; 546/85, 546/86, 87

[56] References Cited

U.S. PATENT DOCUMENTS

| | | | |
|---|---|---|---|
| 4,371,536 | 2/1983 | Braestrup et al. | 546/85 X |
| 4,435,403 | 3/1984 | Braestrup et al. | 546/87 X |
| 4,644,062 | 2/1987 | Haffer et al. | 546/87 X |
| 4,731,358 | 3/1988 | Huth et al. | 546/87 X |
| 4,894,377 | 1/1990 | Braestrup et al. | 514/292 |
| 4,945,090 | 7/1990 | Mogens et al. | 514/232.8 |
| 5,010,077 | 4/1991 | Braestrup et al. | 546/87 X |

FOREIGN PATENT DOCUMENTS

| | | |
|---|---|---|
| 130140 | 6/1984 | European Pat. Off. . |
| 234173 | 11/1986 | European Pat. Off. . |

*Primary Examiner*—Marian C. Knode

*Attorney, Agent, or Firm*—Millen, White, Zelano, & Branigan

[57] ABSTRACT

A process for the production of β-carboline derivatives of general formula I (I)

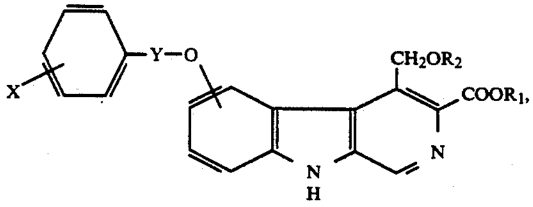

in which

X represents a hydrogen atom or a halogen atom,

Y represents a carbon-oxygen bond or a methyl group, $R_1$ represents an alkyl group with up to 6 carbon atoms and $R_2$ represents an alkyl group with up to 4 carbon atoms, from 1,2,3,4-tetrahydro-β-carboline derivatives of general formula II (II)

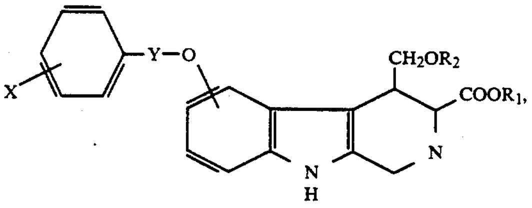

in which

X, Y, $R_1$ and $R_2$ have the above-mentioned meaning, is described, which is characterized in that the 1,2,3,4-tetrahydro-β-carboline derivatives are fermented with a fungi culture of genus Fusarium or Myrothecium.

1 Claim, No Drawings

FERMENTATION PROCESS FOR THE PRODUCTION OF β-CARBOLINE DERIVATIVES BY *MYROTHECIUM VERRUCARIA*

The invention relates to a process for the production of β-carboline derivatives of general formula I (I)

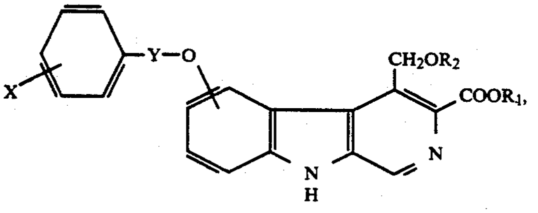

in which

X represents a hydrogen atom or a halogen atom,

Y represents a carbon-oxygen bond or a methyl group, $R_1$ represents an alkyl group with up to 6 carbon atoms and $R_2$ represents an alkyl group with up to 4 carbon atoms, from 1,2,3,4-tetrahydro-β-carboline derivatives of general formula II (II)

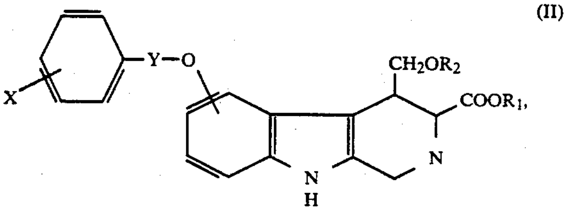

in which

X, Y, $R_1$ and $R_2$ have the above-mentioned meaning.

β-carboline derivatives of general formula I are, as is generally known, pharmacologically effective substances, which can be produced, for example, by chemical dehydrogenation of 1,2,3,4-tetrahydro-β-carboline derivatives of general formula II (EP-A 0130140, EP-A 0234173 and EP-A 0239669). But this chemical dehydrogenation is quite expensive and the yields that can be achieved in this way are low.

It has now been found that the dehydrogenation of 1,2,3,4-tetrahydro-β-carboline derivatives of general formula II can be performed in a simple way under nonpolluting conditions and while achieving satisfactory yields, by these compounds being fermented with a fungal culture of genera Fusarium or Myrothecium. According to the studies so far available, fungal cultures of the species *Myrothecium verrucaria* seem to be especially suitable for the performance of the process according to the invention.

It is very surprising for one skilled in the art that the 1,2,3,4-tetrahydro-β-carboline derivatives of general formula II can be converted with the help of the process according to the invention into β-carboline derivatives of the general formula I since such dehydrogenation on heteroaromatic compounds has not been previously described. The fact that the ester groups of the substrates are not cleaved in this fermentation is also surprising.

The process according to the invention is performed under the same fermentation conditions, which are also used in the known microbiological conversions of substrates with fungal cultures.

Under the culture conditions usually used for fungal cultures, submerged cultures are cultivated in a suitable nutrient medium with aeration. Then, the substrate (dissolved in a suitable solvent or in emulsified form) is added to the cultures and fermented until a maximum substrate conversion is achieved.

Suitable substrate solvents are, for example, methanol, ethanol, glycol monomethyl ether, dimethylformamide or dimethyl sulfoxide. The emulsification of the substrate can be achieved, for example, by the latter being injected in micronized form or dissolved in a water-miscible solvent (such as methanol, ethanol, acetone, glycol monomethyl ether, dimethylformamide or dimethyl sulfoxide) under strong turbulence in (preferably decalcified) water, which contains the usual emulsification aids. Suitable emulsification aids are nonionogenic emulsifiers, such as, for example, ethylenoxy adducts or fatty acid esters of polyglycols. As suitable emulsifiers, the commercially available wetting agents Tegin®, Tween® and Span® can be mentioned as examples.

The optimum substrate concentration, substrate adding time and fermentation period depend on the type of substrate and microorganism and fermentation conditions used. These values, as is generally necessary in microbiological steroid conversions, have to be determined in individual cases by preliminary tests, as they are familiar to one skilled in the art.

The 1,2,3,4-tetrahydro-β-carboline derivatives of general formula II used as initial material for the process according to the invention can have as substituent X, for example, a hydrogen atom or a chlorine atom preferably present in p-position. Suitable substituents $R_1$ of the substrate are, for example, the methyl group, the ethyl group, the propyl group, the isopropyl group or the tert-butyl group. As substituent $R_2$ of the substrates, for example, the ethyl group, the propyl group, the isopropyl group and in particular the methyl group can be mentioned. These compounds are known, or can be produced analogously to the process which is described in EP-A 0130140.

The following embodiment is used for a more detailed explanation of the process according to the invention.

EXAMPLE a) A 2 l Erlenmeyer flask with 500 ml of sterile nutrient medium containing

| | |
|---|---|
| 3 | % glucose |
| 1 | % cornsteep liquor |
| 0.2 | % $NaNO_3$ |
| 0.1 | % $KH_2PO_4$ |
| 0.05 | % KCl |
| 0.002 | % $FeSO_4$ |
| 0.2 | % $K_2HPO_4$ |

with a pH of 6.1 is inoculated with 5 ml of a suspension of a *Myrothecium verrucaria* DSM 2087 culture and shaken for 48 hours at 30° C. with 180 rpm.

b) 20 Erlenmeyer flasks (500 ml) with 100 ml of sterile nutrient medium each containing 1.0 % cornsteep liquor 1.25 % soybean powder adjusted to pH 6.2 are inoculated with 10 ml of *Myrothecium verrucaria* growing culture each and incubated for 7 hours on a rotary shaker with 180 rpm at 30° C.

Then, 0.04 g of 6-benzyloxy-4-methoxymethyl-1,2,3,4-tetrahydro-β-carboline-isopropyl ester dissolved in 1 ml of dimethylformamide and sterilized by filtration is added to each culture and fermented for another 113 hours.

c) The combined cultures are extracted with methyl isobutyl ketone and the extract is concentrated by evaporation under vacuum in a rotary evaporator at a maximum of 50° C. Then, a purification by chromatography on a silica gel column is performed.

0.5 g of 6-benzyloxy-4-methoxymethyl-β-carboline-3-carboxylic acid isopropyl ester of melting point 150°-151° C. is obtained.

We claim:

1. A process for the production of β-carboline derivatives of the formula I

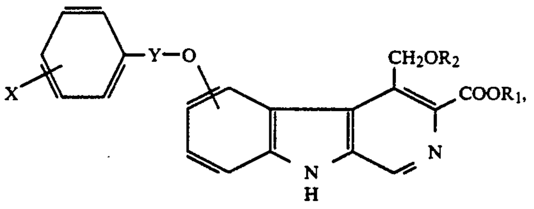

(I)

in which
X represents a hydrogen atom or a halogen atom,
Y represents a carbon-oxygen bond or a methylene group,
$R_1$ represents an alkyl group of 1 to 6 carbon atoms and
$R_2$ represents an alkyl group of 1 to 4 carbon atoms,
from 1,2,3,4-tetrahydro-β-carboline derivatives of the formula II

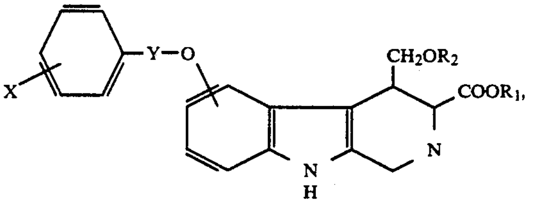

(II)

in which
X, Y, $R_1$ and $R_2$ have the above-mentioned meaning, comprising culturing *Myrothecium verrucaria* in a nutrient medium containing the 1,2,3,4-tetrahydro-β-carboline derivatives under conditions effective to produce the β-carboline derivatives of formula I, and recovering the β-carboline derivatives produced.

* * * * *